United States Patent [19]

Bowen et al.

[11] Patent Number: 5,616,870
[45] Date of Patent: Apr. 1, 1997

[54] PHASE RESOLVED SAMPLING SYSTEM

[75] Inventors: John H. Bowen, Greenfield Center; Jeffery A. Lovett, Scotia, both of N.Y.

[73] Assignee: General Electric Company, Schenectady, N.Y.

[21] Appl. No.: 533,591

[22] Filed: Sep. 25, 1995

[51] Int. Cl.$^6$ .................................................... G01N 1/24
[52] U.S. Cl. .................................. 73/863.01; 73/116
[58] Field of Search ......................... 73/116, 23.3, 23.31, 73/863.01–863.03, 863.82, 864.81

[56] References Cited

U.S. PATENT DOCUMENTS

| | | | |
|---|---|---|---|
| 4,589,292 | 5/1986 | Delhaye et al. | 73/863.03 |
| 5,010,727 | 4/1991 | Cox | 73/116 |
| 5,321,972 | 6/1995 | Stock | 73/23.3 |
| 5,456,124 | 10/1995 | Colvin | 73/116 |

FOREIGN PATENT DOCUMENTS 482539  4/1952  Canada .................. 73/863.82

OTHER PUBLICATIONS

General Valve Corpation, "Iota One—Operating Manual and Set-up Instructions," pp.:1–12, Commercially available product..

*Primary Examiner*—Robert Raevis
*Attorney, Agent, or Firm*—Paul R. Webb, II

[57] ABSTRACT

A system and method periodically sample a fluid stream in a conduit for undergoing analysis thereof. A sampling tube having a probe is joined to the conduit for removing samples from the stream flowing therethrough. An analyzer is joined to the sampling tube for analyzing the removed samples. A solenoid valve is disposed in the tube for controlling flow of the samples to the analyzer. A dynamic pressure transducer is joined to the conduit so that a specific dynamic pressure reference frequency of the stream in the conduit may be locked-on to and used for periodically switching the solenoid valve open and closed for intermittently removing stream samples from the conduit at the reference frequency for channeling to the analyzer periodic stream samples at a sampling frequency corresponding to the reference frequency. In a preferred embodiment, the solenoid valve is switched open at a specific sampling phase in the sampling frequency, which phase may be indexed for obtaining different periodic samples at the sampling frequency for measuring periodic and short duration concentration fluctuations.

15 Claims, 1 Drawing Sheet

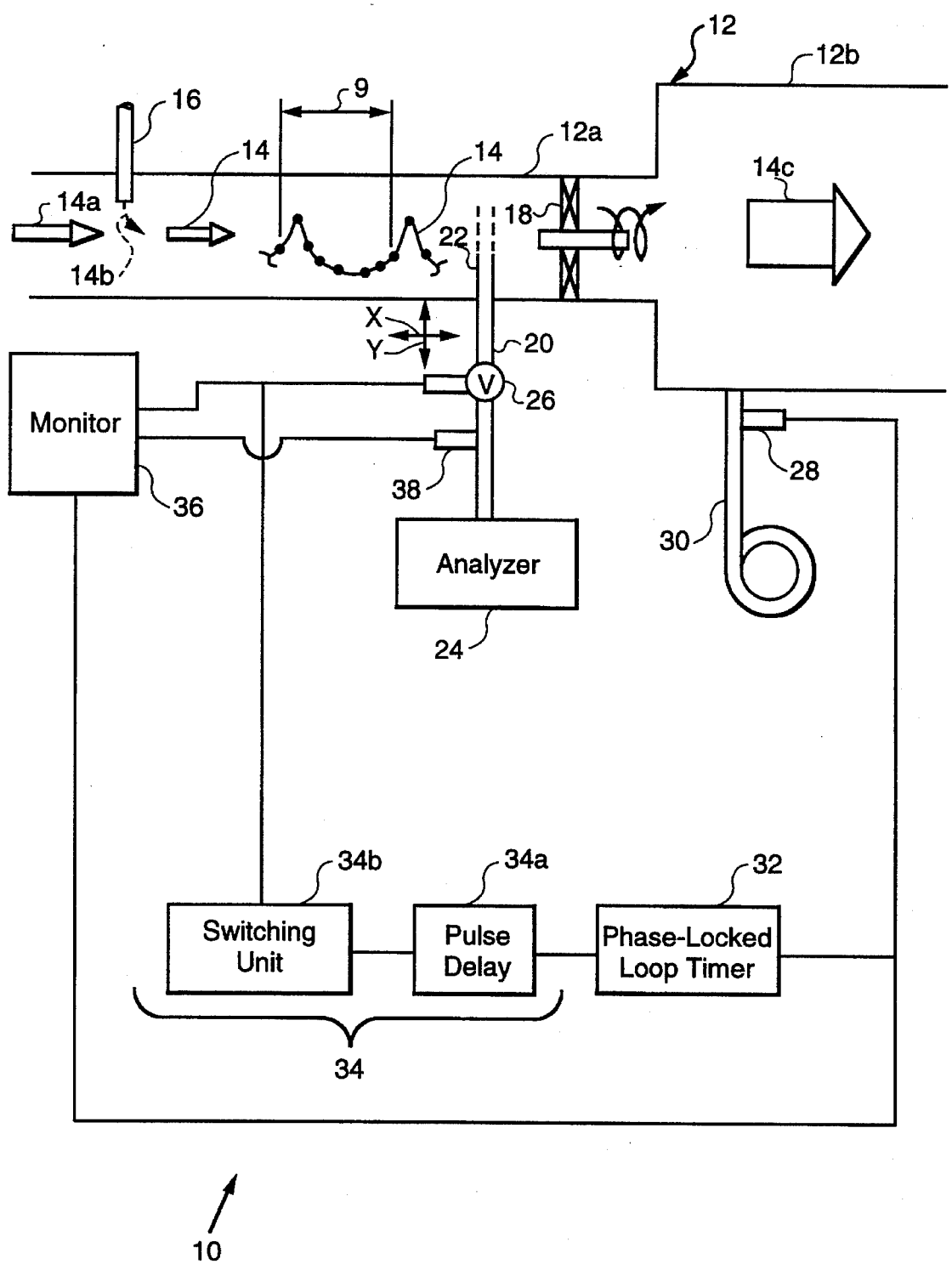

PHASE RESOLVED SAMPLING SYSTEM

BACKGROUND OF THE INVENTION

The present invention relates generally to measurement systems, and, more specifically, to a system for measuring concentration in a fluid stream.

A fluid contained in a vessel may have time varying concentrations of specific components therein. One conventional method of measuring the concentrations therein utilizes a relatively expensive and complex laser system which requires optical access to the fluid for determining the concentrations therein. Operators of the equipment must be specifically trained in its use for obtaining accurate results.

It is desirable to measure time-resolved fuel concentration in a fuel and air mixture in a gas turbine combustor, but a typical laser system is not considered to be practical for this application. For example, low Nox premixed combustors often have limited operability and limited life due to the presence of time-resolved fluid dynamics therein which create dynamic pressure fluctuations which may acoustically excite the combustor and effect undesirably large fatigue stresses. It is therefore desirable to provide a measurement system or tool which may be used in the development of low NOx premixed combustors for measuring the time-resolved concentration of fuel in the air as represented by the fuel/air ratio, the reciprocal of which is also conventionally known as the equivalence ratio. In this way, a better understanding of the coupling between the dynamics of the combustor and its fuel system may be evaluated for improving combustor design and performance and reducing undesirable dynamic behavior.

Accordingly, it is desirable to provide a simple and portable system for measuring time-resolved concentration in a fluid stream, such as in the low NOx premixed combustor, at minimal cost and without visual or optical access being required. The system should also be effective for measuring periodic and extremely short duration fluctuations at the excitation frequencies common in the combustor.

SUMMARY OF THE INVENTION

A system and method periodically sample a fluid stream in a conduit for undergoing analysis thereof. A sampling tube having a probe is joined to the conduit for removing samples from the stream flowing therethrough. An analyzer is joined to the sampling tube for analyzing the removed samples. A solenoid valve is disposed in the tube for controlling flow of the samples to the analyzer. A dynamic pressure transducer is joined to the conduit so that a specific dynamic pressure reference frequency of the stream in the conduit may be locked-on to and used for periodically switching the solenoid valve open and closed for intermittently removing stream samples from the conduit at the reference frequency for channeling to the analyzer periodic stream samples at a sampling frequency corresponding to the reference frequency. In a preferred embodiment, the solenoid valve is switched open at a specific sampling phase in the sampling frequency, which phase may be indexed for obtaining different periodic samples at the sampling frequency for measuring periodic and short duration concentration fluctuations.

BRIEF DESCRIPTION OF THE DRAWINGS

The invention, in accordance with preferred and exemplary embodiments, together with further objects and advantages thereof, is more particularly described in the following detailed description taken in conjunction with the accompanying single drawing figure which is a schematic representation of a phase resolved sampling system in accordance with an exemplary embodiment of the present invention operatively joined to a low NOx premixed combustor for measuring dynamic fuel/air mixture variations.

DESCRIPTION OF THE PREFERRED EMBODIMENT(S)

Illustrated schematically in the sole Figure is a phase resolved sampling system 10 in accordance with an exemplary embodiment of the present invention which is operatively joined to an exemplary vessel or conduit 12 through which a fluid stream 14 is flowing.

In the exemplary embodiment illustrated, the conduit 12 is in the form of a low NOx premixed combustor having an inlet tube 12a joined at its downstream or distal end to a combustion chamber 12b. An upstream or proximal end of the inlet tube 12a receives compressed air 14a from a conventional gas turbine engine compressor (not shown) into which is suitably injected a fuel 14b, such as gaseous methane for example, provided from a conventional fuel injector 16.

A conventional swirler 18 which includes a plurality of circumferentially spaced apart stationary vanes is disposed in the inlet tube 12a at its downstream end adjacent to the combustion chamber 12b for swirling the mixture stream 14 into the combustion chamber 12b wherein it is conventionally ignited for generating combustion gases 14c which flow downstream and are conventionally discharged from the chamber 12b.

The combustor arrangement illustrated in the Figure is merely representative of one type of low NOx premixed combustion which may be analyzed for improving its design during development thereof. Any other type of combustor may also be analyzed, as well as any type of conduit through which flows a fluid stream, the analysis of which is desired.

Low NOx premixed combustors are typically operated very lean and typically have limited operating range and limited life due to the presence of fluid dynamics which must be controlled to prevent undesirable instability thereof during operation which would generate undesirable fatigue stress leading to premature component failure. During operation, the fuel 14b and the air 14a are suitably premixed together in the inlet tube 12a and channeled through the swirler 18 and in turn into the combustion chamber 12b wherein the mixture stream 14 undergoes combustion. Combustion produces dynamic pressure fluctuations which must be controlled for preventing undesirable acoustic or vibratory excitation in the combustion chamber 12b which could adversely affect fatigue life.

In order to understand the operational coupling between the fluid dynamics in the combustion chamber 12b and the fuel system providing the fuel/air mixture stream 14 thereto, it is desirable to provide the relatively simple sampling system 10 which is readily portable and easily joined to the conduit 12 for analyzing dynamic variations in the fuel/air mixture stream 14, and in turn the coupling thereof with the dynamic performance of the combustion chamber 12b due to the combustion gases 14c therein.

As shown in the Figure, the system 10 includes a sampling tube 20 having a suitable probe 22 at a distal end thereof for removing samples of the stream 14 from the conduit 12. In one exemplary embodiment, the probe 12 may simply be in the form of a small orifice in the end of the sampling tube 20 through which a portion of the stream 14 may be withdrawn. The probe 22 is preferably translatable radially within the inlet tube 12a through a sealed access port therein by any conventional means (not shown). In this way, the probe 22 may be positioned at any radial position along the axis Y within the inlet tube 12a for removing stream samples at any radius as desired. The probe 22 is also preferably positionable at various locations along the longitudinal or X axis of the inlet tube 12a, through respective access ports provided therefor, for removing stream samples at different axial positions if desired. In this way, the stream 14 may be sampled at specific radial and axial positions as desired in investigating the coupling between the stream 14 and the dynamic performance of the combustion chamber 12b during operation.

A conventional analyzer 24 is disposed in flow communication with the sampling tube 20 for analyzing the samples removed from the stream 14 by the probe 22 during operation. In the exemplary embodiment illustrated, the fuel 14b is a gaseous fuel such as methane, and therefore, the analyzer 24 is a conventional gas analyzer effective for measuring concentration of the methane fuel 14b in the air 14a for providing a fuel/air ratio.

A conventional, preferably high speed solenoid valve 26 is disposed in serial flow in the sampling tube 20 for controlling flow of the withdrawn samples to the analyzer 24. In order to control operation of the valve 26, a conventional reference dynamic pressure transducer 28 is disposed in flow communication with the combustion chamber 12b for measuring dynamic pressure therein including fluctuations thereof. Since the environment of the combustion chamber 12b is extremely hot during operation, the reference transducer 28 is preferably mounted to the chamber 12b using a conventional damping tube 30 joined at its proximal end to the combustion chamber 12b and having a loop at its distal end configured for damping any resonating dynamic response. The reference transducer 28 is disposed in flow communication adjacent to the proximal end of the damping tube 30 for accurately measuring dynamic pressure within the chamber 12b in a conventional manner. The reference transducer 28 may be mounted in any other suitable manner for accurately recording the dynamic pressure within the chamber 12b during operation, and has its own power supply.

A referencing means 32 in the exemplary form of a conventional phase-locked loop timer is operatively joined to the reference transducer 28 for locking on to a specific dynamic pressure reference frequency of the combustion gas stream 14c in the combustion chamber 12b portion of the conduit 12. The loop timer 32 typically includes a dialing knob for selecting a specific frequency within a larger frequency range of about 0 to 1000 Hertz for example, and also has its own power supply. The loop timer 32 may therefore be used to lock-on to a primary or fundamental dynamic frequency of the combustion gases 14c flowing in the chamber 12b during operation and then generate an electrical signal output trigger pulse once per cycle or period of vibration at the desired reference frequency. In this way, a reference frequency indicative of dynamic performance of the combustion gases 14c during operation may be selected, such as the fundamental or most prominent dynamic response frequency, and locked-on to by the loop timer 32. The loop timer 32 therefore provides a trigger pulse once per period at the reference frequency which is used like a typical strobe light for identifying the repeating period or cycles at a given reference frequency.

Correspondingly, suitable switching means 34 are operatively joined to the loop timer 32 and the solenoid valve 26 for periodically switching open and closed the valve 26 for intermittently removing stream samples from the inlet tube 12a at the reference frequency for channeling to the analyzer 24 periodic stream samples at a sampling frequency corresponding to the reference frequency. In this way, pulsed samples from the inlet tube 12a may be provided to the analyzer 24 at the reference or sampling frequency corresponding to the dynamic behavior being examined in the combustion chamber 12b.

The switching means 34 are preferably effective for switching the valve 26 open at a specific or selected sampling phase repeating at the sampling frequency. For example, the sampling frequency may be 125 Hertz, with the reciprocal thereof providing the time period P for one cycle of 8 milliseconds. One periodic cycle resolves into 360° of phase angle, with the valve 26 being selectively opened for a suitably short duration at a specific phase angle which repeats in cycle-to-cycle as desired. In this way, pulsed samples may be obtained from the stream 14 not only at a specific sampling frequency, but also at a specific phase from cycle-to-cycle at the sampling frequency.

The switching means 34 therefore preferably include a suitable pulse delay circuit or unit 34a operatively joined to the loop timer 32 for receiving the trigger pulse signal therefrom and selectively time delaying the trigger pulse to produce a delayed pulse corresponding to the sampling phase. In this way, the desired sampling phase from 0° to 360° may be simply dialed-in to the delay unit 34a to select the specific sampling phase of interest.

The switching means 34 further include a suitable switching circuit or unit 34b which is operatively joined to the pulse delay unit 34a and the solenoid valve 26 for switching the valve 26 in response to the delayed pulse. In this way, the valve 26 was selectively opened and closed at a desired phase at the sampling frequency for channeling to the analyzer 24 only pulsed samples withdrawn at the precise sampling phase and frequency, with the remaining, non-selected phases not being sampled and collected in the sampling tube 20 downstream of the valve 26.

The pulse delay unit 34a, switching unit 34b, and the solenoid valve 26 may be found in one unit having a suitable power supply therefor. For example, a commercial unit called the "Iota One" is available from the General Valve Corporation of Fairfield, N.J., and is specifically designed for driving molecular beam pulsed sources for laser spectroscopy experiments. The Iota One is readily incorporated into the sampling system 10 illustrated in the Figure in a new use coupled to the reference transducer 28 and analyzer 24 for providing periodic sampling of the stream 14 and analyzing concentrations therein in accordance with sampling phase and frequency.

In the example presented above for a sampling frequency of 125 Hertz, and a cycle period of eight milliseconds, the cycle period may be resolved into eight different sampling points at one millisecond intervals for example. Accordingly, any one of the eight different sampling phases may be selected in the pulse delay unit 34a for repeating from cycle-to-cycle. At each one of the sampling points or phases, the valve 26 remains open for a suitable time such as about 1/10 of the sampling interval, which is about 1/10 of a millisecond for example to withdraw an effective amount of the stream 14.

During operation, a specific sampling phase at a specific sampling frequency may be selected so that the sampling tube 20 upstream of the valve 26 receives only pulsed samples from the stream 14 at repeating points in time relative to dynamic performance in the combustion chamber 12b. By measuring dynamic response in the combustion chamber 12b using the reference transducer 28, the solenoid valve 26 may be operated for periodically removing or sampling samples from the fluid stream 14 in the inlet tube 12a at the desired sapling frequency corresponding to the desired measured dynamic frequency in the combustion chamber 12b. By identifying a fundamental or dominant dynamic frequency in the combustion chamber 12b, for example 125 Hertz, the loop timer 32 may be used to lock-on to that measured frequency which then provides the corresponding or identical sampling frequency of 125 Hertz. The pulsed or periodic samples accumulate in the sampling tube 20 downstream of the valve 26 until they reach a suitable steady state level or quantity so that the analyzer 24 may analyze the collective periodic samples removed from the inlet tube 12a at the sampling frequency. Gas analysis of the collective periodic samples may then indicate the specific fuel/air ratio therefor at the specific sampling phase and frequency.

The pulse delay unit 34a may then be suitably adjusted for selectively indexing the sampling phase to another value within the sampling period at the same sampling frequency for obtaining different periodic samples at the sampling frequency. If the first analysis is performed at a 0° sampling phase, a second analysis may be performed at the next succeeding interval of 45° phase corresponding with one-eight of the sampling period. During the second measurement, the second phase periodic samples are allowed to accumulate in the sampling tube 20 downstream of the valve 26 with the first phase samples being purged from the analyzer 24 as they flow therethrough and are discharged therefrom. After a suitable time period, the second phase periodic samples are allowed to accumulate downstream of the valve 26 and collectively analyzed in the analyzer 24 after reaching a steady state level. In this way, measurements may be made for each desired sampling phase in the sampling period at the sampling frequency either successively in turn or in any other desired order. The order of sampling is not relevant since sufficient time is allowed for the periodic samples collected at desired sampling phases to reach steady state for obtaining meaningful analysis thereof in the analyzer 24.

Illustrated schematically inside the inlet tube 12a in the Figure is a portion of an exemplary curve representing measured fuel/air ratio of the stream 14 as determined by the analyzer 24. One cycle of the sampling frequency is represented by the sampling period P, with there being eight time intervals in each cycle at 45° phase angle between sampling points. In one example tested, variation in fuel/air concentration over a period of eight milliseconds at one millisecond intervals was measured and determined using the invention at the sampling frequency of 125 Hertz. The test results show that for exemplary test conditions, the fuel/air mixture varied in concentration up to about 25% plus and minus from the mean value for the time period. The sampling system 10 in accordance with the present invention is therefore effective for measuring these significant variations in fuel/air mixture throughout a specific sampling period, which would otherwise not be discovered by conventional continuous sampling methods which are effective only for measuring average values over time. The discovered variation in fuel/air mixture in the sampling period may therefore be used for better understanding operation of the combustion chamber 12b and may lead to further advancements in the design of the combustor for reducing undesirable dynamic pressure excitation due to coupling between the fuel/air fluid stream 14 and the combustion gases 14c.

In the exemplary embodiment of the low NOx premixed combustor illustrated, it is preferred that the reference transducer 28 is located on the conduit 12 downstream from the probe 22. In particular, the reference transducer 28 and the corresponding damping tube 30 are joined to the upstream end of the combustion chamber 12b for providing feedback on the dynamic performance at the commencement of the combustion gases 14c during operation. The sampling probe 22 is preferably disposed upstream of the combustion chamber 12b in the inlet tube 12a for periodically sampling the fuel/air mixture stream 14 prior to flow to and combustion in the combustion chamber 14c. In this way, any correlation between dynamic fluctuations in the fuel/air ratio in the stream 14 may be investigated relative to the resulting dynamic performance of the combustion gases 14c and the predominant dynamic pressure frequencies generated thereby.

In order to monitor performance of the sampling system 10, a suitable monitor 36, in the form of a conventional oscilloscope, may be operatively joined to the reference transducer 28 for observing at least its performance. For example, since the predominant dynamic frequency of the combustion gases 14c is typically not known upon commencement of testing, the monitor 36 may be effective for providing a frequency spectrum analysis of the dynamic performance of the combustion gases 14c so that the loop timer 32 may be more quickly adjusted to the proper reference frequency for allowing lock-on thereto. Furthermore, another conventional dynamic pressure transducer 38 may be suitably joined in flow communication with the sampling line 20 between the valve 26 and the analyzer 24, and operatively joined to the monitor 36. In this way, the actual opening and closing of the solenoid valve 26 during operation may be fed back to the monitor 36 for ensuring proper operation of the valve 26 during operation. Accordingly, the solenoid valve 26 may be also operatively joined to the monitor 36 in addition to the switching unit 34b for observing synchronized operation of the feedback transducer 38 with the solenoid valve 26.

The monitor 36 may take any suitable form such as the oscilloscope introduced above, or may be a personal computer based monitoring system for recording all desired useful data in the sampling system 10. The analyzer 24 may have its own visual or print-out data system, or may also be joined to the personal computer data system for storing and presenting the resultant data as desired.

Accordingly, the phase resolved sampling system 10 described above is relatively simple in structure and use for sampling and measuring a fluid stream at a selected sampling frequency and phase angle for discerning periodic variations in the stream itself. Although the system 10 has been described with respect to an exemplary low NOx premixed combustor, it may be used in any application requiring sampling of a fluid stream at specific sampling frequency and phase. The fluid stream 14 may either be a gas or liquid, with the analyzer 24 taking any suitable form for measuring the concentration or variation of any identified component in the stream. The system 10 can be driven by any periodic fluctuation measured within the conduit 12 such as the predominant dynamic pressure frequency found in the combustion gases 14c.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims:

What is claimed is:

1. A system for periodically sampling a fluid stream in a conduit comprising:

a sampling tube having a probe at a distal end for removing samples of said stream from said conduit;

an analyzer disposed in flow communication with said tube for analyzing said samples removed from said stream by said probe;

a solenoid valve disposed in said tube for controlling flow of said samples to said analyzer;

a transducer for measuring dynamic pressure in said conduit;

referencing means operatively joined to said transducer for locking-on to a dynamic pressure reference frequency of said stream in said conduit; and switching means operatively joined to said referencing means and said valve for periodically switching open and closed said valve for intermittently removing stream samples from said conduit at said reference frequency for channeling to said analyzer periodic stream samples at a sampling frequency corresponding to said reference frequency.

2. A system according to claim 1 wherein said switching means are effective for switching said valve open at a specific sampling phase at said sampling frequency.

3. A system according to claim 2 wherein said switching means are effective for indexing said phase for obtaining different periodic samples at said sampling frequency.

4. A system according to claim 3 wherein said referencing means comprise a phase-locked loop timer for locking-on to said reference frequency and producing an electrical trigger pulse once per cycle at said reference frequency for said switching means.

5. A system according to claim 4 wherein said switching means comprise:

a pulse delay unit operatively joined to said referencing means for receiving said trigger pulse and selectively delaying said trigger pulse to produce a delayed pulse corresponding to said sampling phase; and a switching unit operatively joined to said pulse delay unit and said solenoid valve for switching said valve in response to said delayed pulse.

6. A system according to claim 5 further comprising a monitor operatively joined to said transducer for observing performance thereof.

7. A system according to claim 6 further comprising a dynamic pressure feedback transducer disposed in flow communication with said sampling tube between said solenoid valve and said analyzer, and operatively joined to said monitor for observing performance of said solenoid valve.

8. A system according to claim 7 wherein said monitor is an oscilloscope.

9. A system according to claim 3 wherein said transducer is located on said conduit downstream from said probe.

10. A system according to claim 3 wherein said stream includes a gaseous fuel and air mixture, and said analyzer is a gas analyzer for measuring concentration of said fuel in said air.

11. A system according to claim 10 in combination with said conduit, and wherein said conduit comprises:

an inlet tube for channeling said mixture stream; and a combustion chamber disposed in flow communication with said inlet tube for receiving said mixture stream for undergoing combustion in said chamber; and said sampling probe is disposed in said inlet tube; and said transducer is disposed in flow communication with said combustion chamber.

12. A system according to claim 11 further comprising a swirler disposed in said inlet tube adjacent to said combustion chamber for swirling said mixture stream 14 into said combustion chamber, and said sampling probe is disposed upstream of said swirler.

13. A method for periodically sampling a fluid stream in a conduit comprising:

removing periodically samples of said stream from said conduit;

analyzing said samples removed from said stream;

controlling flow of said samples for analyzing;

measuring dynamic pressure in said conduit;

locking-on to a dynamic pressure reference frequency of said stream in said conduit; and intermittently removing stream samples from said conduit at said reference frequency for analyzing said stream samples at a sampling frequency corresponding to said reference frequency.

14. A method according to claim 13 wherein said samples are periodically removed from said conduit at a specific sampling phase in said sampling frequency.

15. A method according to claim 14 further comprising indexing said sampling phase for obtaining different periodic samples at said sampling frequency.

\* \* \* \* \*